United States Patent [19]

Reime

[11] Patent Number: 4,773,405
[45] Date of Patent: Sep. 27, 1988

[54] APPARATUS AND METHOD APPLYING STRAIGHTENING AND TWISTING FORCES TO LIMBS

[75] Inventor: Roy O. Reime, Gilroy, Calif.

[73] Assignee: Progressive Engineering, a Partnership, Gilroy, Calif.

[21] Appl. No.: 940,602

[22] Filed: Dec. 11, 1986

[51] Int. Cl.$^4$ ............................................. A61F 5/04
[52] U.S. Cl. .................................................. 128/80 B
[58] Field of Search ................ 128/80 A, 80 B, 80 C, 128/80 F, 80 G, 80 R; 128/87 C, 84 A

[56] References Cited

U.S. PATENT DOCUMENTS

| 173,051 | 2/1876 | Parke | 128/87 R |
|---|---|---|---|
| 874,446 | 12/1907 | Slater | 128/87 R |
| 1,384,257 | 7/1921 | Hilgers | 128/80 B |
| 1,630,108 | 5/1927 | Buckowitz | 128/80 B |
| 2,308,776 | 1/1943 | Peckham | 128/80 B |
| 2,357,323 | 9/1944 | Goldberg | 128/84 R |
| 2,630,116 | 3/1953 | Leathers | 128/80 B |
| 4,576,151 | 3/1986 | Carmichael et al. | 128/80 R |

FOREIGN PATENT DOCUMENTS

| 1552131 | 11/1968 | France | 128/80 R |
|---|---|---|---|
| 251960 | 11/1911 | Fed. Rep. of Germany | 128/80 B |
| 354533 | 6/1922 | Fed. Rep. of Germany | 128/80 B |
| 482764 | 9/1929 | Fed. Rep. of Germany | 128/80 B |
| 2239382 | 2/1974 | Fed. Rep. of Germany | 128/80 F |
| 496032 | 3/1976 | U.S.S.R. | 128/80 C |

OTHER PUBLICATIONS

Journal of Medical Engineering and Technology, pp. 100–102, vol. 1, No. 2 (Mar. 1977).

Primary Examiner—Charles A. Pearson
Assistant Examiner—Tonya Lamb
Attorney, Agent, or Firm—Limbach, Limbach & Sutton

[57] ABSTRACT

An apparatus and method for the orthopedic treatment of a leg or other limb having a joint between its proximal and distal portions. Saddles are secured to the proximal and distal portions of the limb. A compression strut is secured between the saddles to the rearward side of the limb. A stay is secured between the proximal saddle and a saddle secured to and extending around the rearward side of the distal portion of the limb. The stay may be adjusted laterally relative to the saddles secured thereto whereby twisting force may be applied to the limb. Compression pads are disposed between the stay and the limb to either side of the joint whereby, together with the saddles, straightening forces may be selectively applied to the limb.

10 Claims, 3 Drawing Sheets

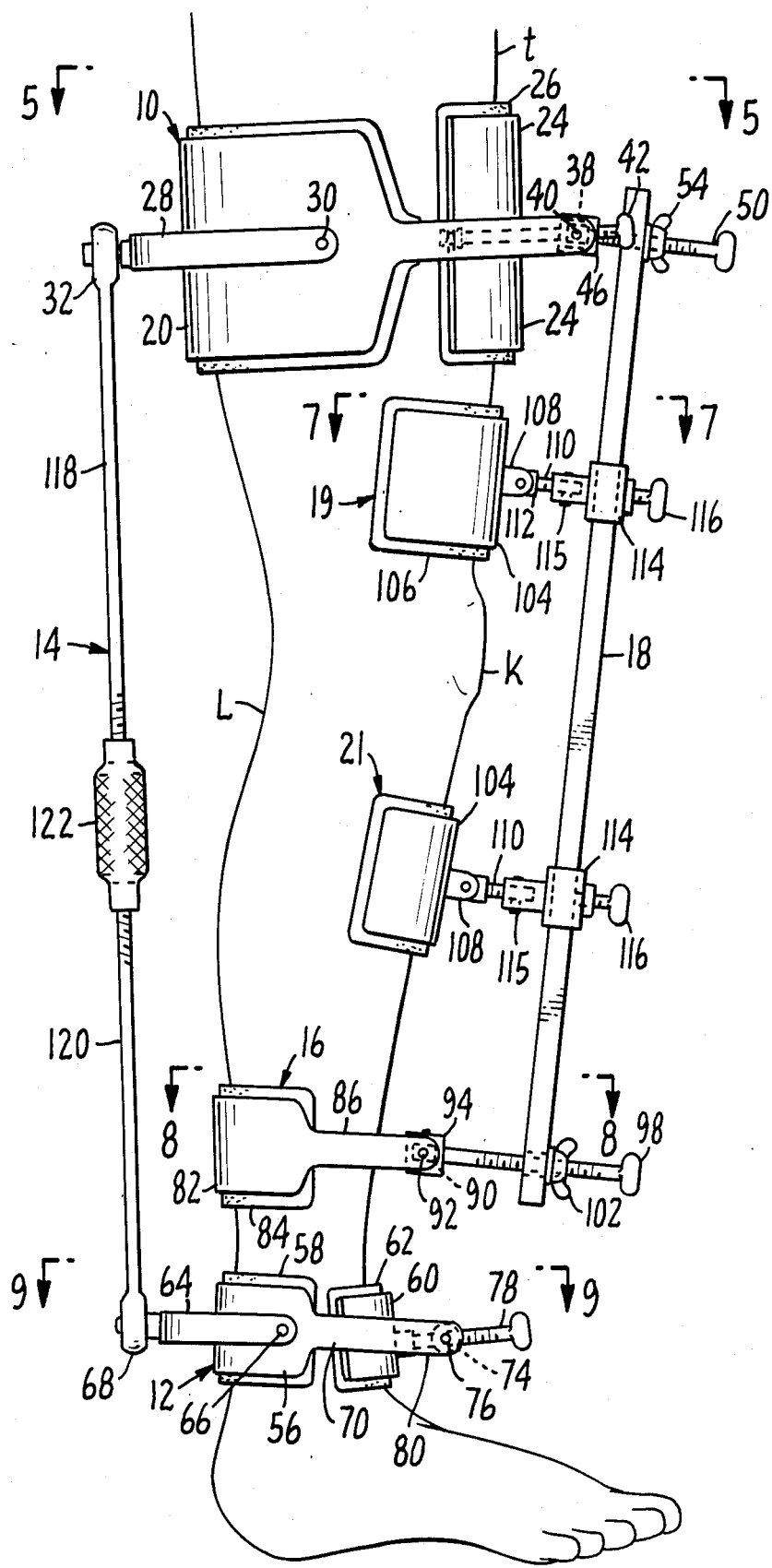
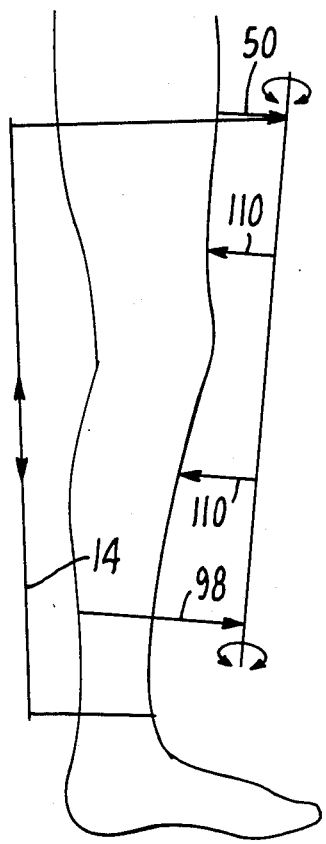
FIG. 1.
FIG. 2.

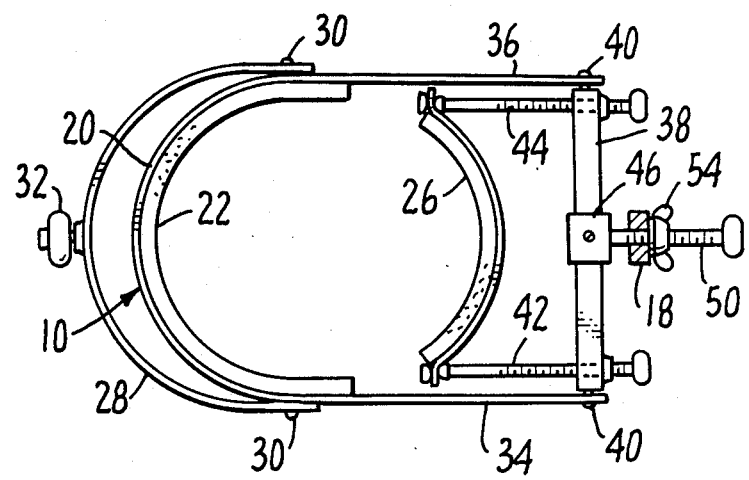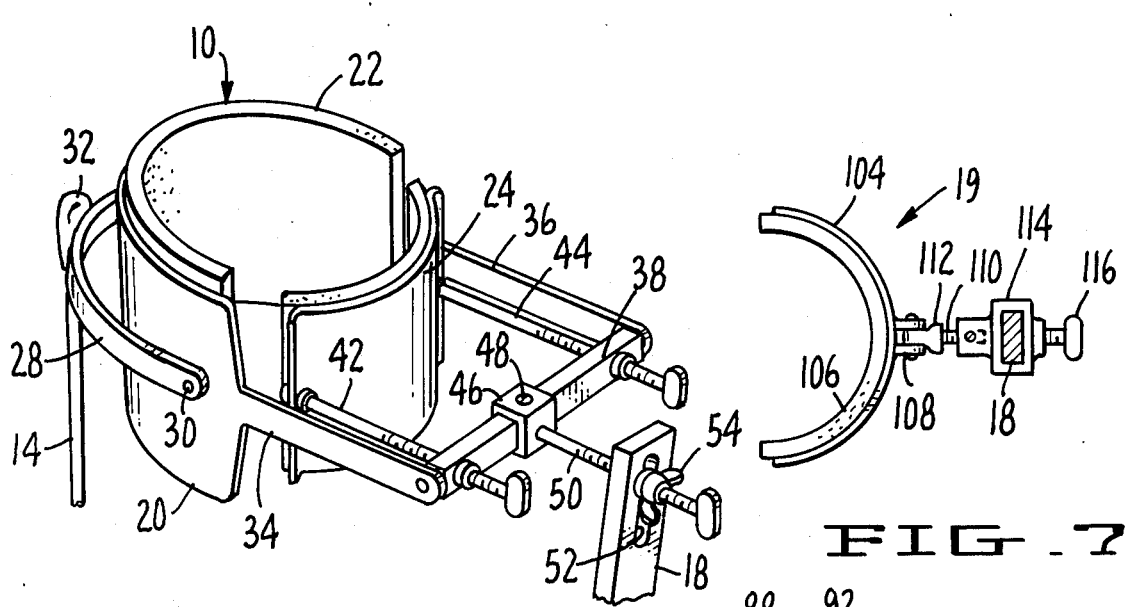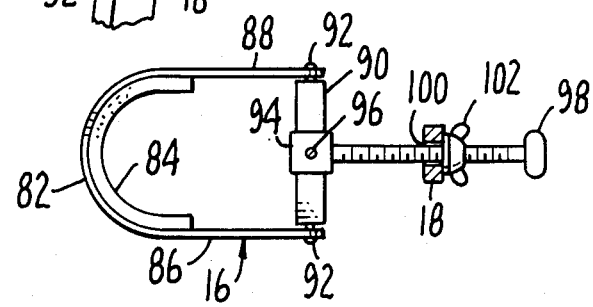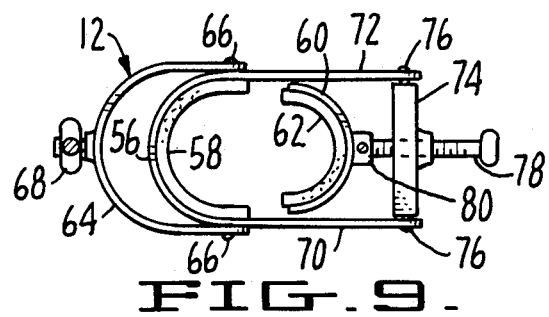

4,773,405

APPARATUS AND METHOD APPLYING STRAIGHTENING AND TWISTING FORCES TO LIMBS

BACKGROUND OF THE INVENTION

The present invention relates to a method and apparatus for the orthopedic treatment of the leg or other limbs of the body and, more particularly, is concerned with a method and apparatus which may be used for therapeutic purposes to promote the correction of knee or leg damage. In its more specific aspects, the invention is concerned with a brace which may be selectively adjusted to impart tension, compressive pulling, and twisting forces to the limb being treated and may be adjusted at any time to maintain the positions required to promote corrective therapy.

The most common type of prior art device used to maintain the position of injured limbs is the fixed cast. Casts are typically applied to the limb of a patient for a given period of time to maintain the limb in a fixed condition. They have the disadvantage that they provide no adjustment once in place and that they encapsulate the limb during treatment so that it may not be observed. The tendons in a limb immobilized by a cast tend to shrink as well as diminish, thereby creating a bend in the limb when it is removed from the cast. In the case of leg treatment, the bend may be to a backward position as much as 30° from straight.

In addition to casts, various types of adjustable orthopedic devices have been provided. U.S. Pat. Nos. 2,357,323 and 3,788,307 teach straightening by means of pads which may be extended and retracted by screw adjustments. 1920 German Patent No. 337,258 teaches a mechanism which may be applied to the legs of a patient to apply lateral forces thereto. U.S. Pat. No. 874,446 shows an extensible surgical splint, and 1948 Italian Patent No. 442,755 shows an extensible rod-like orthopedic apparatus, together with pads which may be extended. U.S. Pat. No. 173,051 teaches tensioning by means of an extensible rod parallel to the leg of the patient, and U.S. Pat. No. 2,295,253 suggests an apparatus which may be used to align fractured bones.

While the foregoing patents are representative of the prior art, they do not teach the unique combination of the present invention, and particularly an apparatus and method which provides for the combined application of tension forces, compressive forces, pulling forces, and twisting forces.

SUMMARY OF THE INVENTION

The brace of the present invention comprises proximal and distal saddles adapted to be engaged with a limb, such as the leg, to either side of the joint therein. A stay is secured between the saddles and adapted to be positioned to the forward side of the limb. Compression imparting means are secured to the stay and adapted to be engaged with the forward side of the limb to either side of the joint to, together with the saddles, impart straightening forces to the limb. Twisting forces may be applied to the limb by laterally adjusting the positions at which the proximal and distal saddles are secured relative to the stay. In a preferred embodiment, the brace also includes a compression strut secured between the proximal saddle and a distal saddle and adapted to be positioned to extend longitudinally of the limb to impart tension forces thereto.

The method of the invention provides for the orthopedic treatment of a limb having proximal and distal portions with a knee joint therebetween. In the practice of the method, saddles are secured to said proximal and distal portions and a stay is extended between the saddles to the forward side of the limb. Through pads, the stay is used for imparting compressive forces to the forward side of the limb to either side of the knee joint as the saddles are pulled toward the stay. In a preferred embodiment, the method further comprises extending a strut between the saddles to impart tension forces to the limb.

A principle object of the present invention is to provide a method and apparatus which may be employed to selectively and adjustably impart tension, compression, pulling and twisting forces to a leg.

Another object of the invention is to provide such a method and apparatus which may be used in place of a full leg cast or in combination with a small leg cast so that a full leg cast may not be required.

Still another object of the invention is to provide such a method and apparatus which enables the limb being treated to be visually observed at all times and which does not fully envelope the limb.

Yet another object of the invention is to provide such a method and apparatus which does not completely immobilize the patient being treated.

Yet a further object of the invention is to provide such a method and apparatus which may be readily tailored to accommodate patients of different sizes.

These and other objects will become more apparent from the following detailed description and the accompanying drawings.

BRIEF DESCRIPTION OF THE DRAWINGS

FIG. 1 is a side elevational view of the apparatus, as applied to the leg of a patient;

FIG. 2 is a side elevational view of the leg of a patient, with an overlying force diagram showing the forces which may be imparted to the leg by the apparatus and method;

FIG. 5 is a cross sectional view of the apparatus, taken on the plane designated by line 5—5 of FIG. 1;

FIG. 6 is a perspective view, with parts thereof broken away, illustrating the proximal or top-most saddle of the apparatus;

FIGS. 7, 8 and 9 are cross sectional views of the apparatus, taken on the planes designated by lines 7—7, 8—8, and 9—9, respectively, of FIG. 1.

DESCRIPTION OF THE PREFERRED EMBODIMENT

Figure 3:
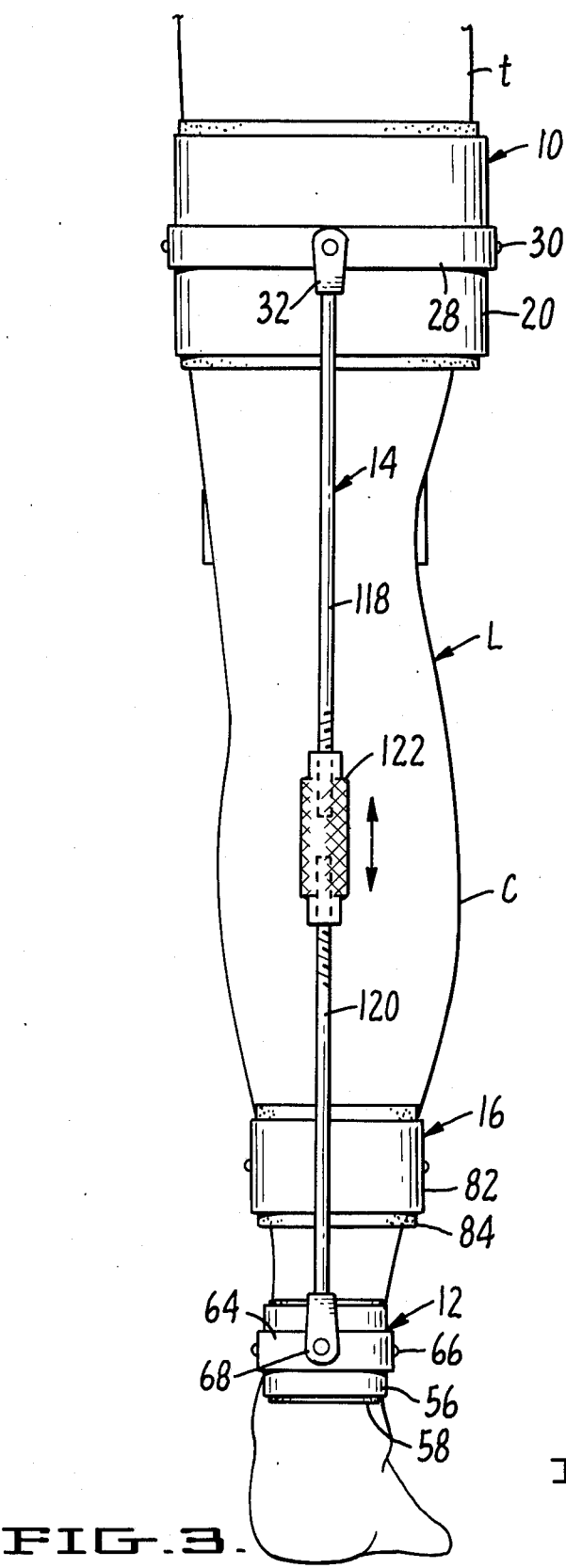
FIGS. 3 and 4 are rear and front elevational views, respectively, of the apparatus as applied to the leg of a patient.

Referring now to the drawings, the leg of a patient is designated therein in its entirety by the letter "L". The knee joint of the leg is designated by the letter "k". The proximal or thigh portion of the leg is designated by the letter "t", and the distal or calf portion of the leg is designated by the letter "c".

The apparatus of the invention is shown applied to the leg L and comprises: a first or proximal saddle 10 secured around the thigh portion t; a second or distal saddle 12 secured around the ankle at the distal end of the calf portion c; a compression strut 14 secured between the saddles 10 and 12 and extending longitudinally of the leg L to the rearward side thereof; a secondary distal saddle 16 extending around the rearward side of the calf portion c; a stay secured between the saddles 10 and 16 to the forward side of the leg L; and compression pads 19 and 21 secured between the stay 18 and the leg L to either side of the knee k.

The saddle 10, as may best be seen from FIGS. 1 and 6, comprises: a primary arcuate plate 20 proportioned for engagement about the rearward side of the thigh portion t, said plate being lined with a resilient pad 22; a secondary arcuate plate 24 proportioned for engagement with the forward side of the thigh portion t, said plate being lined with a resilient pad 26, a yoke 28 pivotally secured to the sides of the plate 20 through pin connections 30, said yoke being pivotally secured to the compression strut 14 via swivel connection 32; a pair of arms 34 and 36 integrally joined to the sides of the plate 20 and extending forwardly therefrom; a transverse bar 38 extending between the arms 34 and 36 and pivotally secured thereto by releasable pin connections 40; a pair of compression bolts 42 and 44 extending threadably through the bar 38 to swivel connections with the plate 24 whereby the bolts may be used to adjust the position of the plate 24 relative to the bar 38; a slide 46 slidably received on the bar 38 for a slidable movement relative thereto, said slide carrying a set screw 48 engageable with the bar 38 to selectively lock the slide relative to the bar; a wing bolt 50 secured to and extending forwardly from the slide 46 through a slot 52 in the stay 18; and, a wing nut 54 threadably received on the bolt 50 for engagement with the stay 18.

The saddle 12 is of a construction similar to that of the saddle 10, except that it is not secured to the stay 18 and is not provided with structure to provide for such securement. The elements of the saddle 12 comprise: a primary arcuate plate 56 having a resilient lining pad 58; a secondary arcuate plate 60 having a resilient lining pad 62; a yoke 64 pivotally secured to the sides of the plate 56 by pin connections 66 and pivotally secured to the strut 14 by a swivel 68; a pair of arms 70 and 72 integrally joined to the plate 56 and extending forwardly therefrom; a transverse bar 74 pivotally secured between the arms 70 and 72 by (See FIGS. 4 and 9) releasable pin connections 76; and a wing bolt 78 extending threadably through the bar 74 to a swivel connection 80 with the plate 60.

The secondary distal saddle 16 engages only the rearward side of the leg and comprises: an arcuate plate 82 lined with a resilient pad 84; a pair of arms 86 and 88 integrally joined to the plate 82 and extending forwardly therefrom; a transverse bar 90 extending between the arms 86 and 88 and secured thereto by releasable pin connections 92; a slide 94 slidably received on the bar 90, said slide carrying a set screw 96 selectively engageable with the bar 90 to lock the slide against movement relative to the bar; a wing bolt 98 secured to the slide 94 and extending slidably through a slot 100 formed in the say 18; and, a wing nut 102 threadably received on the bolt 98 for engagement with the stay 18.

The compression pads 19 and 21 are of the same construction and each comprise: an arcuate plate 104 having a resilient lining pad 106; a pair of ears 108 fixed to the outside of the plate 104; a bolt 110 having a flattened boss 112 at one end thereof pivotally secured between the ears 108 and a slide block 114 threadably secured to the other end thereof in slidable engagement with the stay 18; a set screw 115 extending through the slide block 114 for engagement with the bolt 110; and, a set screw 116 threadably received in the slide block 114 for engagement with the stay 18 to selectively lock the slide block 114 relative to the stay.

The compression strut 14 takes the form of a pair of rods 118 and 120 secured at their distal ends to the swivels 32 and 68 and at their inner ends to a turnbuckle 122. The turnbuckle 122 provides means whereby the strut may be selectively lengthened or shortened to vary the tension applied to the leg of the patient.

The apparatus of the invention is tailored to the size of the patient to be treated. This tailoring entails choosing the lengths of the strut 14 and stay 18, as well as the radii of the various saddle and pad members. Dimensions are chosen so that the apparatus will assume a condition generally as shown in FIG. 1 when in place on a patient.

The apparatus is applied to the leg of the patient with the elements which are to be disposed to the forward and rearward sides of the legs released from one another. The released condition is provided through means of the releasable pin connections 40, 76 and 92. In applying the apparatus, typically the elements to the back of the leg would be placed first and then the elements to the front of the leg would be positioned and the pin connections snapped into place. Then the secondary arcuate plates 24 and 60 would be adjusted through means of the screw mounts therefore to securely engage the leg. Such engagement functions to secure the saddles 10 and 12 in place. Once the saddles are so in place, the wing bolt 98 for the arcuate plate 82 may be adjusted to apply the desired tension to the distal saddle 16 and the pads 19 and 21 may be adjusted to impart the desired compression to the forward side of the leg. The latter adjustment is facilitated by screwing the screws 110 into or out of the slide blocks 114. During the course of setting up the apparatus, the turnbuckle 122 is also adjusted to impart the desired tension to the leg and the slides 46 and 94 are adjusted relative to the transverse support bars therefore to impart the desired degree, if any, of twisting to the leg.

The force diagram shown in FIG. 2 illustrates the various forces which are selectively applied to the leg through the aforementioned adjustment technique. There it will be seen that the strut 14 imparts tension to the leg, the bolts 50 and 98 pull the proximal and distal portions of the leg forwardly, and the bolts 110 impart compressive force to the forward side of the leg to either side of the knee.

Figure 4:
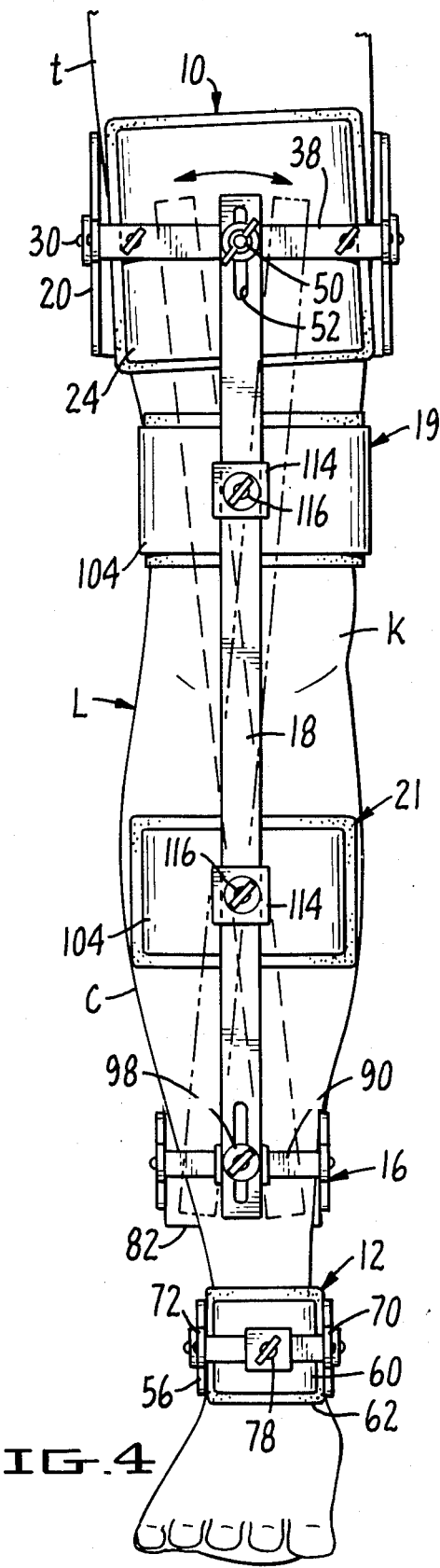

FIGS. 3 and 4 also diagrammatically illustrate the manner in which the apparatus functions to apply tension and twisting forces to the leg of a wearer. From FIG. 3, it will be seen that the strut 14 applies tension to the leg through means of the saddles 10 and 12. FIG. 4 shows how the stay 18 may be adjusted transversely relative to the bars 38 and 90 to impart twisting force to the leg. The solid line representation of the stay 18 illustrates the apparatus in a condition where no significant twisting is applied to the leg of the patient. The phantom line representations of the stay diagrammatically illustrate how the apparatus may apply twisting force to the leg of the wearer in either lateral direction. From FIG. 4 it will also be seen that the bolts 50 and 98 extend through slots in the stay 18 and that these slots accommodate some degree of longitudinal adjustment of the saddles 10 and 16 relative to the stay. Similarly, the slide blocks 114 permit longitudinal adjustment of the pads 19 and 21 relative to the stay 18.

It will be appreciated that the various bolts, wing nuts and set screws, as well as the turnbuckle 122, all facilitate both adjustment of the apparatus and function to secure the apparatus in adjusted condition. By the same token, these adjustable connections enable the apparatus to be adjusted during therapy. For example, where the apparatus is used to straighten a leg which has been immobilized in a cast for a period of time, adjustment may be gradually carried out over a period of days, weeks or months to gradually move the leg to a straight condition. It should also be appreciated that the apparatus leaves the foot of the patient free so that, providing the leg has sufficient strength, he may walk with the apparatus in place.

CONCLUSION

From the foregoing description, it is believed apparent that the present invention enables the attainment of the objects initially set forth herein. In particular, it provides an apparatus and method whereby the limb of a patient may be selectively subjected to tension, twisting and compressive forces and these forces may be adjusted as the condition of the patient changes. It should be understood, however, that the invention is not intended to be limited to the specifics of the illustrated embodiment, but rather as defined by the accompanying claims.

I claim:

1. A brace and tensioning device for the orthopedic treatment of a limb having proximal and distal portions with a knee joint therebetween, said device comprising:
   a first saddle adapted to be secured to the proximal portion;
   a second saddle adapted to be secured to the distal portion;
   a compression strut secured between said first and second saddles and adapted to be positioned to the rearward side of the knee joint;
   a third saddle adapted to be secured to the distal portion and embrace the rearward side thereof;
   a stay secured between said first and third saddles and adapted to be positioned to the forward side of the knee joint; and
   compression imparting means secured to the stay and adapted to be engaged with the forward side of the limb to either side of the knee joint.

2. A device according to claim 1 further comprising means to selectively adjust the length of the compression strut.

3. A device according to claim 1 or 2 wherein the first and third saddles are secured to the stay through means providing for the selective lateral adjustment of said saddles relative to the stay.

4. A device according to claim 1 wherein the compression imparting means are selectively extensible relative to the stay to vary the degree of compression imparted to the limb thereby.

5. A device according to claim 1 or 4 further comprising means to selectively and adjustably move the first and third saddles toward and away from the stay.

6. A device according to claim 1 or 4 wherein the stay is elongate and adapted to extend longitudinally of the limb and the compression imparting means are selectively movable along the length of the stay to adjust the points of engagement between said means and the limb.

7. A device according to claim 6 wherein the compression imparting means comprise pads secured to the stay and engageable with the limb to either side of the knee joint.

8. A device according to claim 1 wherein the first and second saddles include elements adapted to embrace the forward and rearward sides of the limb to which said saddles are secured.

9. A device according to claim 1 or 8 wherein said first and second saddles are secured to the strut through swivels.

10. A method for the orthopedic treatment of a limb having proximal and distal portions with a knee joint therebetween, said device comprising:
    securing a first saddle about the proximal portion;
    securing a second saddle about the distal portion;
    securing a compression strut between said first and second saddles to the rearward side of the knee joint;
    securing a third saddle to the distal portion in a condition the rearward side thereof;
    securing a stay between said first and third saddles to the forward side of the knee joint; and
    imparting compressive force to the forward side of the limb to either side of the knee joint through said stay simultaneously with the imparting of straightening force to the rearward side of the limb through the stay and the saddles secured thereto.

* * * * *